United States Patent
Upadhya et al.

(10) Patent No.: US 11,172,882 B2
(45) Date of Patent: Nov. 16, 2021

(54) MONITORING SYSTEM

(71) Applicant: Vital Connect, Inc., San Jose, CA (US)

(72) Inventors: Ashwin Upadhya, San Jose, CA (US);
Frank Pan, San Jose, CA (US)

(73) Assignee: Vital Connect, Inc., San Jose, CA (US)

( * ) Notice: Subject to any disclaimer, the term of this patent is extended or adjusted under 35 U.S.C. 154(b) by 188 days.

(21) Appl. No.: 16/121,772

(22) Filed: Sep. 5, 2018

(65) Prior Publication Data
US 2020/0069252 A1    Mar. 5, 2020

(51) Int. Cl.
*A61B 5/00*    (2006.01)
*G06F 1/3206*    (2019.01)
*A61B 5/08*    (2006.01)

(52) U.S. Cl.
CPC .......... *A61B 5/6813* (2013.01); *A61B 5/0006* (2013.01); *A61B 5/0816* (2013.01); *G06F 1/3206* (2013.01)

(58) Field of Classification Search
CPC ..... A61B 5/6813; A61B 5/006; A61B 5/0816; A61B 5/0205; G06F 1/3206
See application file for complete search history.

(56) References Cited

U.S. PATENT DOCUMENTS

| | | | |
|---|---|---|---|
| 2015/0346799 A1 | 12/2015 | Sengupta et al. | |
| 2015/0347287 A1* | 12/2015 | Tripathi | G06F 1/3206 |
| | | | 711/154 |
| 2017/0086054 A1 | 3/2017 | Azevedo et al. | |

OTHER PUBLICATIONS

International Search Report and Written Opinion from International Application No. PCT/US2019/049439 dated Dec. 30, 2019.

* cited by examiner

*Primary Examiner* — Joseph M Dietrich
(74) *Attorney, Agent, or Firm* — Brundidge & Stanger, P.C.

(57) ABSTRACT

A wearable device includes one or more sensors of information from a subject. The wearable device may have an electronic assembly supported by a base. The electronic assembly may include a sensor data collection system configured to control collection of sensor data related to one or more characteristics of a subject and one or more processors. the sensor data collection system may include a controller configured to control sequencing and scheduling of the sensor data collection, and a buffer configured to receive and buffer data corresponding to the sensor data collected from the one or more sensors in accordance with a signal provided by the controller. The one or more processors may be configured to receive the buffered data from the buffer in accordance with a wake signal; process the received data; and output the processed data. Scheduling and sequencing the sensor data collection by the sensor data collection system may be decoupled from the processor such that the processor may be in a low-power sleep mode during data collection and in a normal power mode to process data received from the buffer.

17 Claims, 6 Drawing Sheets

MONITORING SYSTEM

TECHNICAL FIELD

The present invention relates to monitoring, and more particularly, to health monitoring by a wearable device utilizing low-power, on-device processing.

BACKGROUND

Monitoring systems are used in a variety of applications including monitoring the health of individual subjects. Some monitoring systems, including some health monitoring systems, include a combination of underlying systems or device components such as sensors, recording systems, and storage units. Software may be integrated with the hardware of one or more device components to aid the communication of data between device components or between a device component and an external component, such as a display, server, analyzer, network, etc.

Some monitoring systems also may have processing systems and associated components to process the data, including data analysis in some instances. However, such monitoring systems commonly employ a processor to control most or all aspects of the data collection and processing, and are thus prone to high power consumption and issues related thereto, potentially including reduced battery life, excessive heat generation, high sampling jitter, maximum achievable bandwidth, and unpredictable timing of events related to the sensor data collection and processing.

Therefore, there is a need for a monitoring system that addresses the above and other issues by reducing power consumption associated with, at least, data collection and processing. The present disclosure addresses this and other needs.

SUMMARY OF THE DISCLOSURE

In a first aspect, a monitoring system may comprise a sensor data collection system configured to control collection of sensor data related to one or more characteristics of a subject, including: a controller configured to control sequencing and scheduling of the sensor data collection, and a buffer configured to receive and buffer data corresponding to the sensor data collected from the one or more sensors in accordance with a signal provided by the controller; and one or more processors configured to: receive the buffered data from the buffer in accordance with a wake signal, process the received data; and output the processed data, wherein scheduling and sequencing the sensor data collection by the sensor data collection system is decoupled from the processor.

In a second aspect, a wearable device may comprise a base and an electronic assembly supported by the base, wherein the electronic assembly includes: a sensor data collection system configured to control collection of sensor data related to one or more characteristics of a subject, including: a controller configured to control sequencing and scheduling of the sensor data collection, and a buffer configured to receive and buffer data corresponding to the sensor data collected from the one or more sensors in accordance with a signal provided by the controller: and one or more processors configured to: receive the buffered data from the buffer in accordance with a wake signal, process the received data, and output the processed data, wherein scheduling and sequencing the sensor data collection by the sensor data collection system is decoupled from the processor.

BRIEF DESCRIPTION OF THE DRAWINGS

The accompanying figures, together with the written disclosure, serve to illustrate embodiments of a monitoring system. One of ordinary skill in the art will recognize that the particular embodiments illustrated in the figures are merely exemplary and are not intended to limit the scope of the present invention.

DETAILED DESCRIPTION

The present disclosure relates to a monitoring system and, more particularly, to devices and systems configured for reduced-power sensor data collection and processing in the field of health monitoring. The following description is presented to enable one of ordinary skill in the art to make and use the disclosed embodiments and modifications thereof, and is provided in the context of a patent application and its requirements. Various modifications to the disclosed embodiments and the principles and features described herein will be readily apparent to those of ordinary skill in the art. Thus, the present disclosure is not intended to limit the invention to the embodiments shown; rather, the invention is to be accorded the widest scope consistent with the principles and features described herein.

Figure 1:
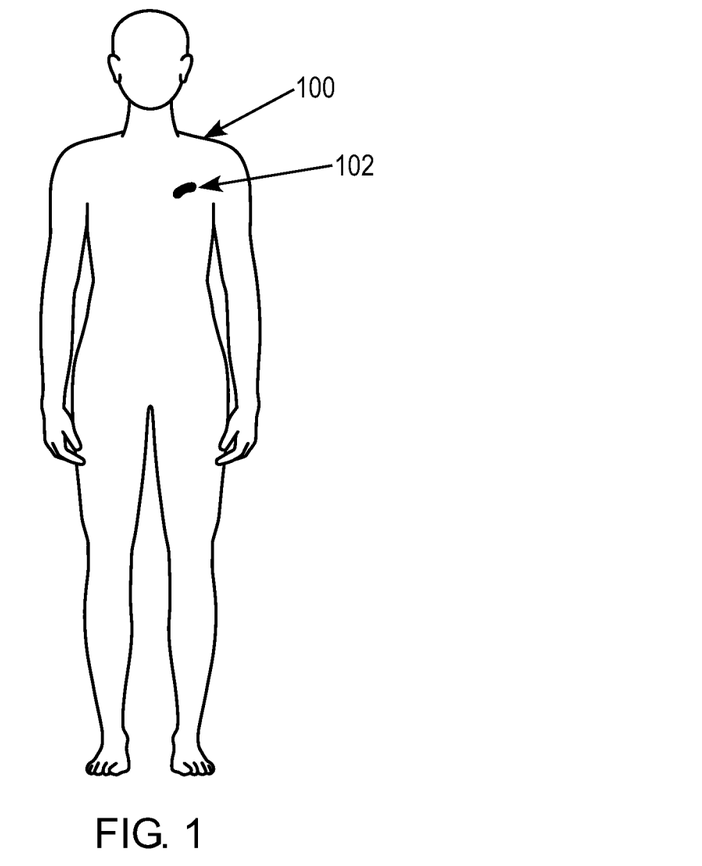
FIG. 1 illustrates an example of a subject (e.g., patient) wearing a wearable device.

FIG. 1 illustrates an example of a subject (e.g., patient) 100 wearing a wearable device 102. Wearable device 102 may be positioned at any location suitable for its monitoring function or functions. For example, and without limitation, the location may be a region of the upper torso. A specific location suitable for monitoring certain conditions may include any of the left midclavicular line over intercostal space (ICS) 2 in a modified lead-II configuration, vertically over the upper sternum, and horizontally on the left midclavicular line over ICS 6. In any these and other locations, when appropriately configured, wearable device 102 may be utilized to monitor physiological characteristics or qualities related to subject 100 including but not limited to ECG and accelerometer signals. To this and other ends, wearable device 102 may include hardware, firmware, and/or software to perform various sensing, processing, and transmitting of information related to the subject 100, as discussed more fully below.

Figure 2A:
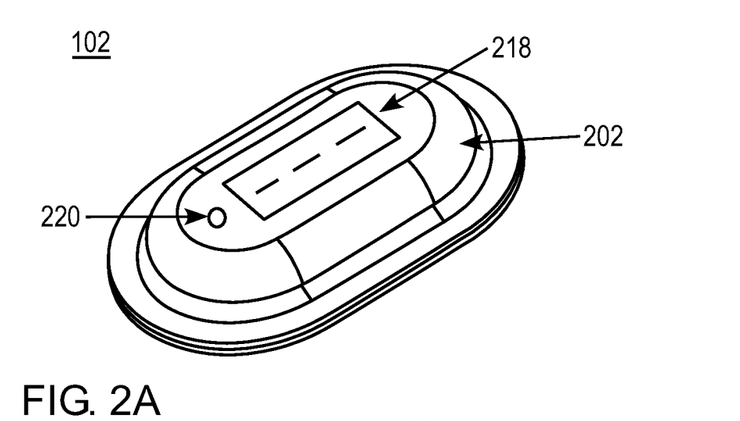
FIG. 2A illustrates a wireless sensor device in accordance with one or more embodiments described herein.
Figure 2B:
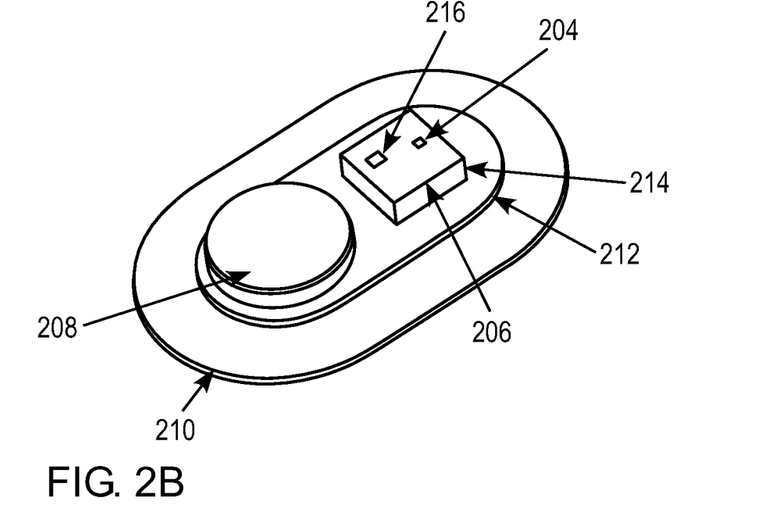
FIG. 2B illustrates an isometric view of the wireless sensor device of FIG. 2A with a top cover removed, in accordance with one or more embodiments described herein.
Figure 2C:
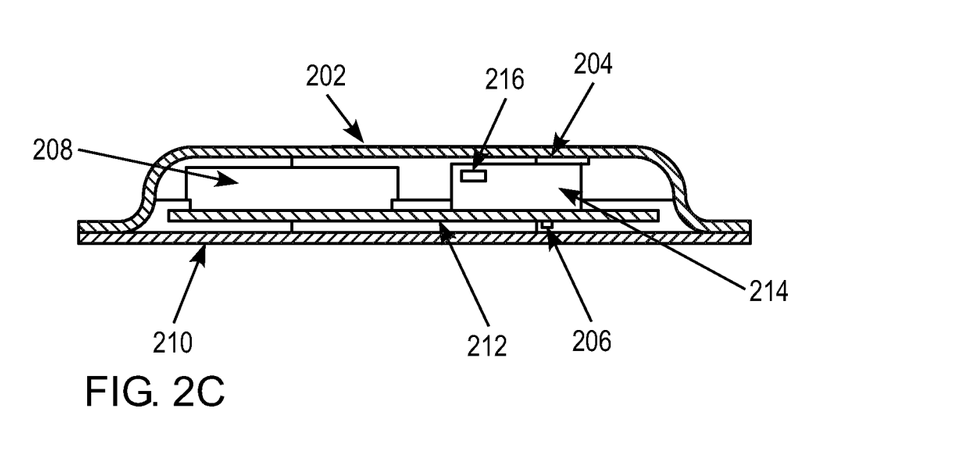
FIG. 2C illustrates a cross-section view of the wireless sensor device illustrated in FIG. 2A and components thereof illustrated in FIG. 2B, in accordance with one or more embodiments described herein.

FIGS. 2A-2C collectively illustrate a nonlimiting example of wearable device 102 as a wireless sensor device configured with one or more sensors to detect characteristics and/or qualities of subject 100. More particularly, FIG. 2A illustrates a wireless sensor device in accordance with one or more embodiments described herein, FIG. 2B illustrates an isometric view of the wireless sensor device of FIG. 2A with a top cover removed, in accordance with one or more embodiments described herein, and FIG. 2C illustrates a cross-section view of the wireless sensor device illustrated in FIG. 2A and components thereof illustrated in FIG. 2B, in accordance with one or more embodiments described herein.

In some embodiments, wearable device 102 may be disposable and/or reusable In the example shown in FIGS. 2A-2C, wearable device 102 may include a cover 202, one or more sensors (sensors 204 and 206 are illustrated), a battery 208, a base 210, a spacer 212, electronic circuitry 214, a transmitter or transceiver 216, a display 218, and a speaker 220. Some components related to or necessary for the functioning of the illustrated components may not be shown for clarity. Furthermore, indications of such components are illustrative in nature and not necessarily to absolute or relative scale or form. Electronic components within wearable device 102, such as some or all electronic components and related structure inside the device when cover 202 is in place, may be termed an "electronic assembly" elsewhere in this description. The electronic assembly may include a processing system and sensor data collection system, which are discussed below. The electronic assembly or parts thereof may be disposable and/or reusable relative to or with cover 202 and/or base 210.

In one or more embodiments, wearable device 102 may be attached to subject 100 via base 210 by, e.g., a skin-friendly adhesive or other device. Sensors 204, 206 may be in direct contact with subject 100 or separated from subject 100 by base 210 or other component(s) or device(s). Although two sensors are shown, wearable device 102 may have one sensor or more than two sensors. Spacer 212 may include a suitable insulating material to physically and/or electrically separate elements such as electronic circuitry 214 and sensor 206 or base 210, and additional insulating material may be employed instead of or together with spacer 212 for such a purpose. Such insulating material may include air, foam and/or Polyetheretherketone (PEEK) for insulation, for example.

In general, sensors 204 and 206 are configured and placed to obtain data from subject 100. Such data is processed by wearable device 102, for example by a processor system-on-chip, to obtain data by any combination of analog, digital, and/or algorithmic processes. (Hereinafter, usage of "process" may include "analysis" with respect to data; these terms thus may be used in combination, singly, interchangeably, or in the alternative as context dictates or permits.) The obtained data may be stored in a memory on wearable device 102 or transmitted externally by transmitter/transceiver 216 as desired. According to at least one embodiment, the processor may execute instructions to process the data and obtain information regarding the subject, such as conditions related to the subject's health. The processed data or information may be displayed via display 218 of wearable device 102. (Hereinafter, "data" or "information" may be used in combination, singly, interchangeably, or in the alternative as context dictates or permits.) Additionally or alternatively, the processed information may be provided to transmitter/transceiver 216 and, in turn, be transmitted externally to a user or device for any suitable purpose, such as information gathering, further processing, user or machine analysis, and/or storage. By way of nonlimiting example, transmitter/transceiver 216 may transmit information such as physiological signals after analysis or in raw form to a remote device/server (e.g. a terrestrial or cloud-based server, or a mobile device such as a smartphone or tablet (not shown in FIG. 1)). Information also may be provided in an audible form, such as a verbal report or nonverbal signal (e.g., alert).

One of ordinary skill in the art readily recognizes that a variety of sensors can be utilized as or in addition to sensors 204 and 206 described above, including but not limited to temperature sensors; respiratory sensors; sensors of heart, brain, and other organ activity; body position accelerometers (e.g., tri-axial accelerometers, uni-axial accelerometers, bi-axial accelerometers, and/or gyroscopes); and/or pressure sensors, the use of all of which would be within the spirit and scope of the present disclosure. One of ordinary skill in the art will also readily recognize that details of the electronic assembly, other electrical components, form factor, structural and electrical configuration, materials, etc. are illustrative and that various modifications of the same may be made in accordance with such factors as patient size, configuration, and comfort; physical environment; cost, etc. All such variations and modifications are considered within the spirit and scope of this disclosure.

Figure 3:
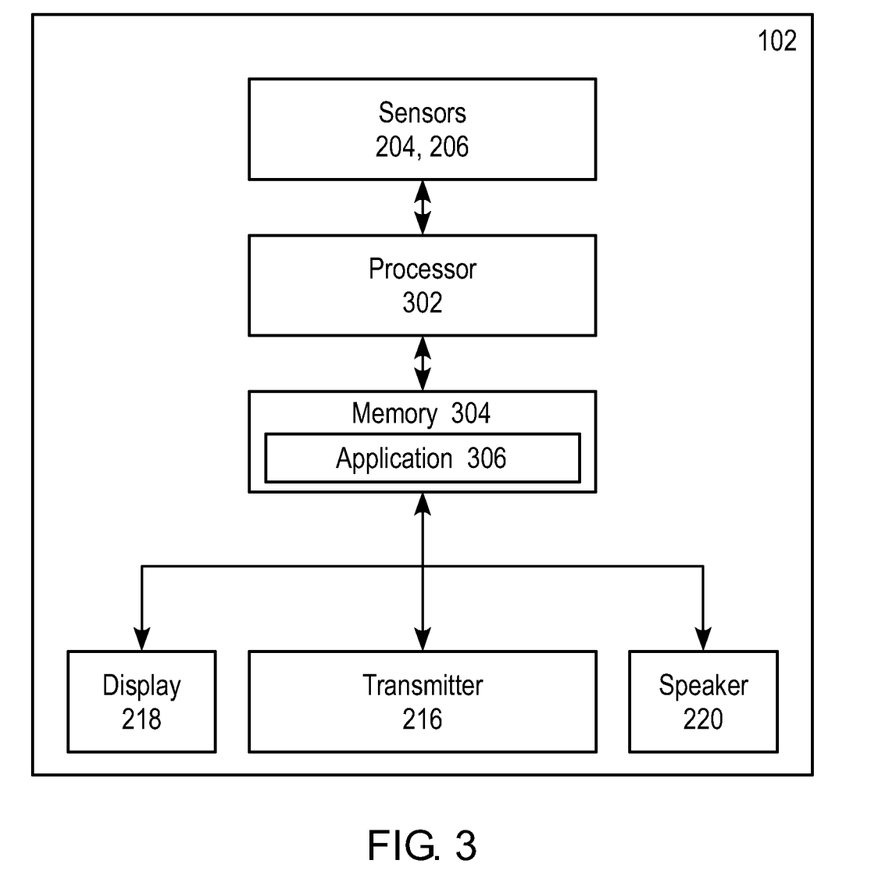
FIG. 3 is a block diagram schematically illustrating basic elements that may comprise one or more embodiments of a wearable device.

FIG. 3 is a block diagram schematically illustrating basic elements that may comprise one or more embodiments of wearable device 102. As shown, wearable device 102 may include sensor 204, 206 to detect information, e.g., at least one physiological signal from subject 100; a processor 302 operably coupled to receive data collected from sensors 204, 206; and a memory 304 coupled to the processor, wherein memory 304 may store an application 306 including instructions that, when executed by the processor, cause the processor to perform operations related to the information detected by sensors 204, 206. Such operations may, for example, include processing and/or analyzing the collected data to determine a condition of subject 100 and/or derive information that, if provided to a user or other device, conveys information that can be used to determine a condition of subject 100. One of ordinary skill in the art will readily conceive of myriad uses for such information and operations to be performed by processor 302 to provide the same.

Operations related to detecting information by the sensors, collecting data from the information and providing the data to processor 302, executing application 306, and outputting the processed or related information via transmitter/transceiver 216, display 218, and/or speaker 220 are controlled by sequencing and scheduling schemes according to various clocks. Some such schemes rely heavily on processor 302 to control, collect, and process the sensor data which, while having some advantages, nevertheless may be prone to issues related to high power consumption such as reduced battery life, excessive heat generation, high sampling jitter, maximum achievable bandwidth, and unpredictable timing of events related to the sensor data collection and processing, to name a few.

Figure 4:
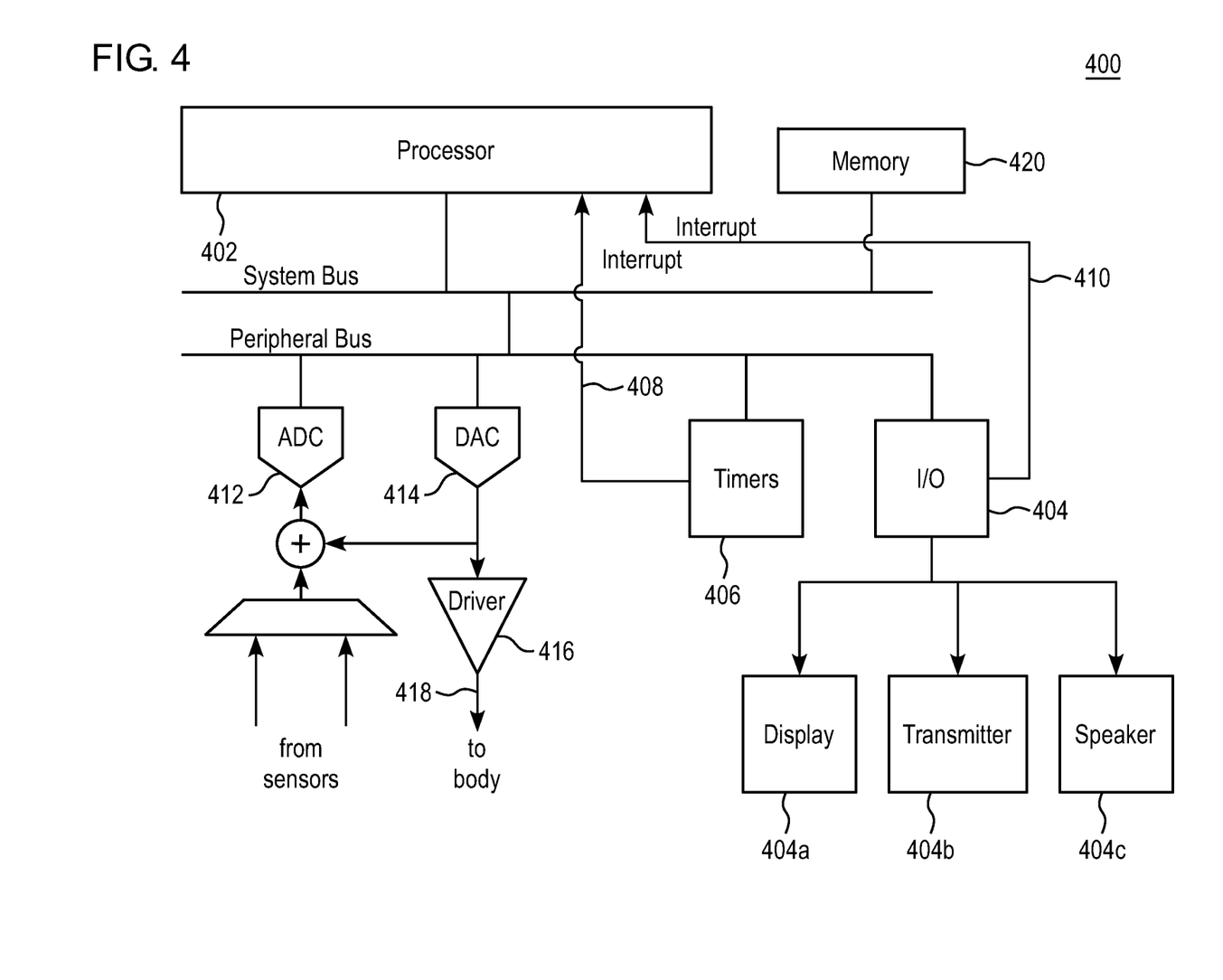
FIG. 4 shows a block diagram illustrating features of a monitoring system.

FIG. 4 shows a block diagram illustrating features of one such system. As shown, a system 400 may use a processor 402 to control, acquire, and process data from multiple sensors. These systems may schedule timing critical events related to sensor data collection and processing of the sensor data and data of peripherals such as a display 404a, a transmitter/transceiver 404b, or a speaker 404c via I/O interface(s) 404, for example using a combination of timers 406 and interrupts 408, 410. In the illustrated system, sensor data may be analog data converted to digital data using an analog-to-digital converter (ADC) 412, and processed data output from processor 402 may be digital data output to one or more peripherals and/or converted to analog data via a digital-to-analog converter (DAC) 414. The output of DAC 414, via a driver 416, may provide the subject with a signal 418 to detect or permit measurement of a physiological sign or to stimulate a response, both of which may be sensed and input to ADC 412 as discussed above. For example, signal 418 may cause light to be generated in a pulse oximeter, the output of which may be input to ADC 412.

Timing related to critical events and priorities (e.g., sensor selection, ADC triggering, buffering, data write/read, instruction processing, etc.) rely on accurate synchronization, and complex systems such as system 400 may have multiple such critical events and priorities, which may lead to uncertainty in timing of the events. In addition, such systems are inherently inefficient in power. Processor 402 and a memory 420, which may store application instructions for execution by processor 402, may be a significant part of the system in terms of transistors/gates. System 400 may thus run at a high system clock frequency and suffer significantly high dynamic and static power consumption.

Also, as processor 402 is responsible for controlling and processing data of multiple sensors, the maximum bandwidth achievable for the system may be limited by high power consumption and few available processor cycles for data acquisition and processing.

To address these and other issues, scheduling, sequencing, and data acquisition management may be decoupled from (i.e., not performed by) the processor. Instead, power to the processor and its operation can be managed synchronously with, e.g., data collection such that data may be collected and stored in the background during a low-power processor time. For example, a clock setting a power supply to the processor can be shut down during (decoupled) data collection and, when a desired amount of data has been collected and/or stored, power is supplied to activate (e.g., "wake up") the processor to process the data and then shut down again when the processing is complete. A block diagram illustrating this and other features is shown schematically in FIG. 5.

Figure 5:
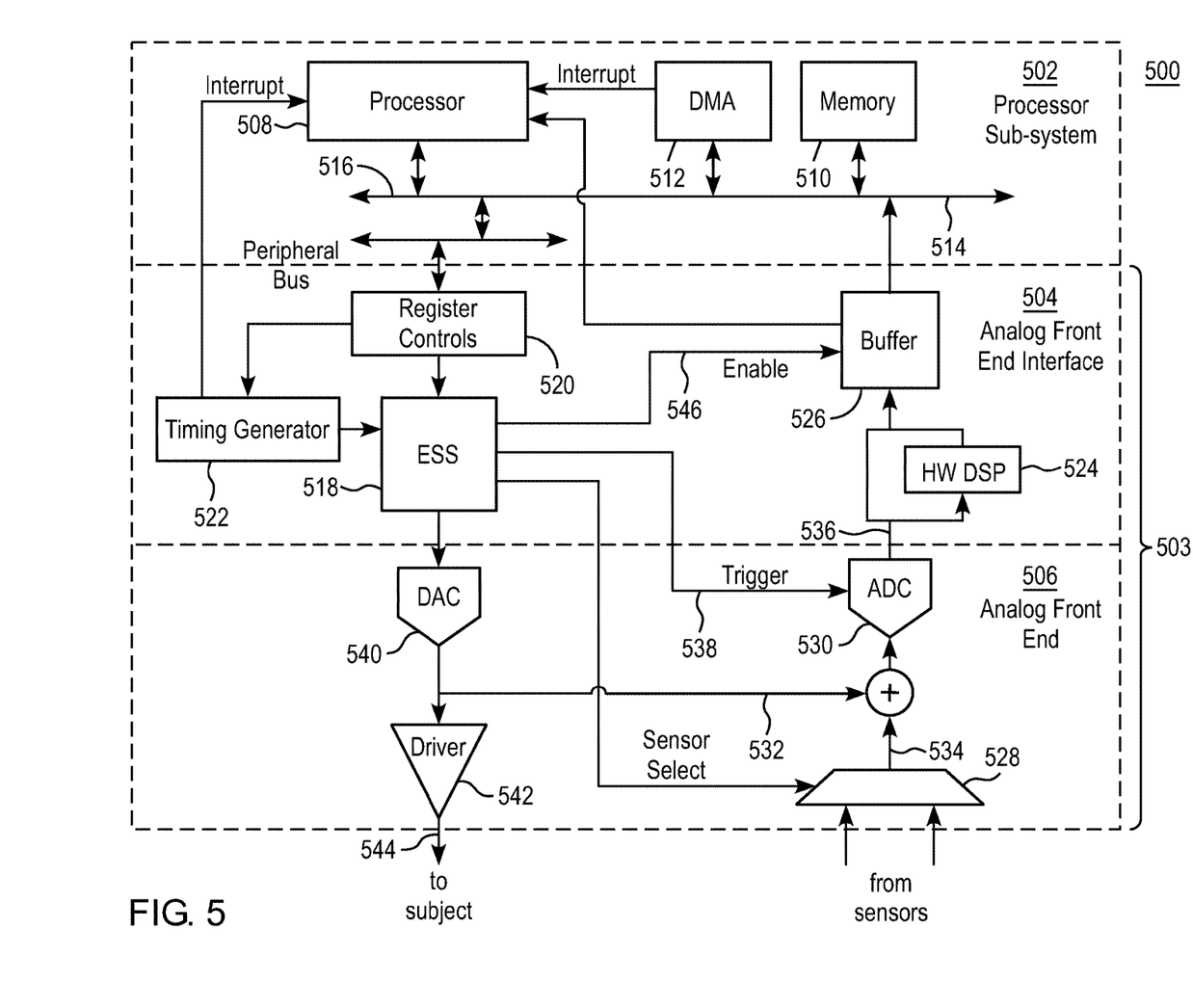
FIG. 5 shows a block diagram of elements of a monitoring system in which certain functions may be decoupled from a processor, in accordance with one or more embodiments described herein.

FIG. 5 shows a block diagram of elements of a monitoring system in which certain functions may be decoupled from a processor, in accordance with one or more embodiments described herein. For example, system 500 may be a System-on-Chip (SoC) capable of use with wirelessly connected sensory devices such as a wireless wearable device 102. As illustrated, system 500 may include a processor sub-system 502 and a sensor data collection system 503 comprising an analog front end (AFE) interface 504 and an analog front end (AFE) 506.

In some embodiments, processor sub-system 502 may include may include a processor 508, a shared system memory 510 (e.g., a static random access memory (SRAM) chip), a memory controller 512 (e.g., a direct memory access (DMA) controller), a system bus 514, and a peripheral bus 516. Processor 508, system memory 510, and memory controller 512 are shown coupled to system bus 514. If system 500 is configured as an SoC, some of the foregoing components or other components may be provided on- or off-chip, although for convenience of description such components may be described herein as being components of system 500.

In one or more embodiments, AFE interface 504 may include a programmable event sequencer and scheduler (ESS) 518 coupled to system bus 514 via register controls 520 and peripheral bus 516, a timing generator 522, an optional hardware digital signal processor (DSP) 524, and a buffer 526.

In one or more embodiments, processor 508 may be a microprocessor that controls configuration and communication tasks. Processor 508 is shown decoupled from sensor scheduling, sequencing, and data acquisition, thereby allowing processor 508 to enter a low-power mode (e.g., "sleep"), through a SLEEP instruction or otherwise, while ESS 518 manages the sensor scheduling, sequencing, and data collection. When in sleep mode, one or more clocks to processor 508 may be turned off, excluding interface modules, for example. In some embodiments, these exclusions may be switched on independently of clock gating selection in order to keep processor 508 behaving normally to incoming requests. To awaken processor 508 from low-power mode, for example when a desired amount of sensor information has been collected or buffer 526 is full, buffer 526 may provide a wake signal to processor 508. Another determinant for waking processor 508 may be employed. Once awake, processor 508 or memory controller 512 can retrieve data from buffer 526 for processing.

In one or more embodiments, DSP 524 may be a microprocessor operating in either single processor mode or, with processor 508, in dual processor mode. DSP 524 may perform signal processing-intensive tasks when in dual processor mode, for example. When in single processor mode, DSP 524 may perform both control/communications and signal processing. DSP 524 is also capable of being set to a sleep mode.

In one or more embodiments, AFE 506 may include a selector 528 configured to receive analog sensor data and controllably output the analog data to an ADC 530 according to a sensor select signal 532 from ESS 518. ADC 530 may be configured to receive the selected analog data 534, convert analog data 534 to digital data 536, and output digital data 536 to buffer 526 (optionally via DSP 524) in accordance with a trigger signal 538 from ESS 518.

In one or more embodiments, processed data output from processor 508 may be digital data output to one or more peripherals via peripheral bus 516 and/or converted to analog data via a DAC 540 via ESS 518. The output of DAC 540, via a driver 542, may provide the subject with a signal 544 to detect or permit measurement of a physiological sign or to stimulate a response, both of which may be sensed and input to ADC 530 as discussed above. For example, signal 544 may cause light to be generated in a pulse oximeter, the output of which may be input to ADC 530. In some embodiments, the output of DAC 540 may be fed back to the output of selector 528 to improve the signal-to-noise ratio of the input to ADC 530.

Sensory information may be output via suitable peripheral interfaces. For example and without limitation, two SPI (serial peripheral interface) master interfaces may be provided, one dedicated for the SPI flash and another to access SPI slaves on MEMs (microelectromechanical systems), gyroscopes etc. Two UART interfaces also may be provided, one for Bluetooth Low Energy (BTLE) access and another debug access, by way of nonlimiting example. Further, an I2C master interface may be provided for Altimeter access. One of ordinary skill in the art will understand and be able to implement these and other interfaces as needed.

In one or more embodiments, system 500 may operate in two power domains—a "VDD" domain and a "VDD_SW" domain. The VDD domain may be an Always-ON domain whereas the VDD_SW may be switched to a low-power SLEEP-state to reduce dynamic and static power, for example.

In some embodiments, the VDD domain may include one or more of clock control, reset control, power-management, and the AFE interface. The processor subsystem, peripherals, and other components, one or more of which may be within the core block, may be in the VDD_SW domain. By having the AFE interface in the "Always-ON" domain, the SoC has the capability to go to a low-power state while still being able to capture data from the AFE.

In some embodiments, the sequencing of events from Normal Power mode (ON-mode) to Low Power mode (SLEEP-mode) may be managed by ESS 518. When in NORMAL mode, processor 508 may set up and synchronize timers and the wake-up. For example, processor 508 may enable a down-counting timer along with a master-timer, allowing the down-counting timer and master-timer to be in sync. SLEEP mode may be entered when the down-counting timer expires. Other determinants may be used to cause SLEEP mode, including but not limited to an interruption of sensor data collection or end of data retrieval from buffer 526.

During SLEEP mode ESS 518, ADC interface, DAC interface and power management may be at regular VDD and continue to operate as before. In one or more embodiments, NORMAL power mode may resume in accordance with expiration of a sleep timer and/or a trigger. For example, a sleep timer may begin to count down from a preloaded value and NORMAL mode may resume when the sleep timer expires. In one or more embodiments, NORMAL mode may resume in response to a trigger, which may be an external interrupt as from a MEMS or BTLE device, from a buffer 526 Almost-Full flag or a battery-brownout signal. The countdown of the sleep timer may begin in accordance with the trigger.

In one or more embodiments, on entering SLEEP mode, a clock to the core may be turned "OFF". When the sleep timer expires or in response to an external interrupt, the clock to the core may be turned "ON", and processor 508 may continue from where it was held.

ESS 518 may be a time-driven sequencer to perform a sequence of "events." Within each "event", multiple instructions and triggers can be scheduled, including but not limited to writing analog and digital control registers, triggering DAC 540 and ADC 530 at programmed times; passing a time stamp received from timing generator 522 at an identifiable trigger to buffer 526 to identify, e.g., when data is captured at selector 528 or an event happened; identifying ADC streams in accordance with the trigger to distinguish data by sensor; etc. ESS 518 also may enable one or more core components to be in low-power while it manages the AFE data capturing.

Thus, with processor 508 in low-power mode or otherwise, ESS 518 can manage scheduling, sequencing, and data acquisition. For example, FIG. 5 shows ESS 518 controlling sensor selection with sensor select signal 532, ADO output with trigger 538, and data write to buffer 528 with data_wr signal 546. ESS 518 itself may be operably coupled to timing generator 522, and ESS 518 and timing generator 522 may be coupled to system bus 514 via register controls 520. Timing generator 522 may act as a reference clock for timings provided by ESS 518 and, because ESS 518 can have a small instruction memory, ESS 518 may be programmable and maintain accurate timing in accordance with the reference clock provided by timing generator 522, while consuming less power than a system under single processor control such as system 400. In particular, the sum of power consumed by ESS 518 and processor 508 in performing their operations as part of wearable device 102 may be less than the power consumed by processor 402 in performing similar operations if part of wearable device 102.

Figure 6:
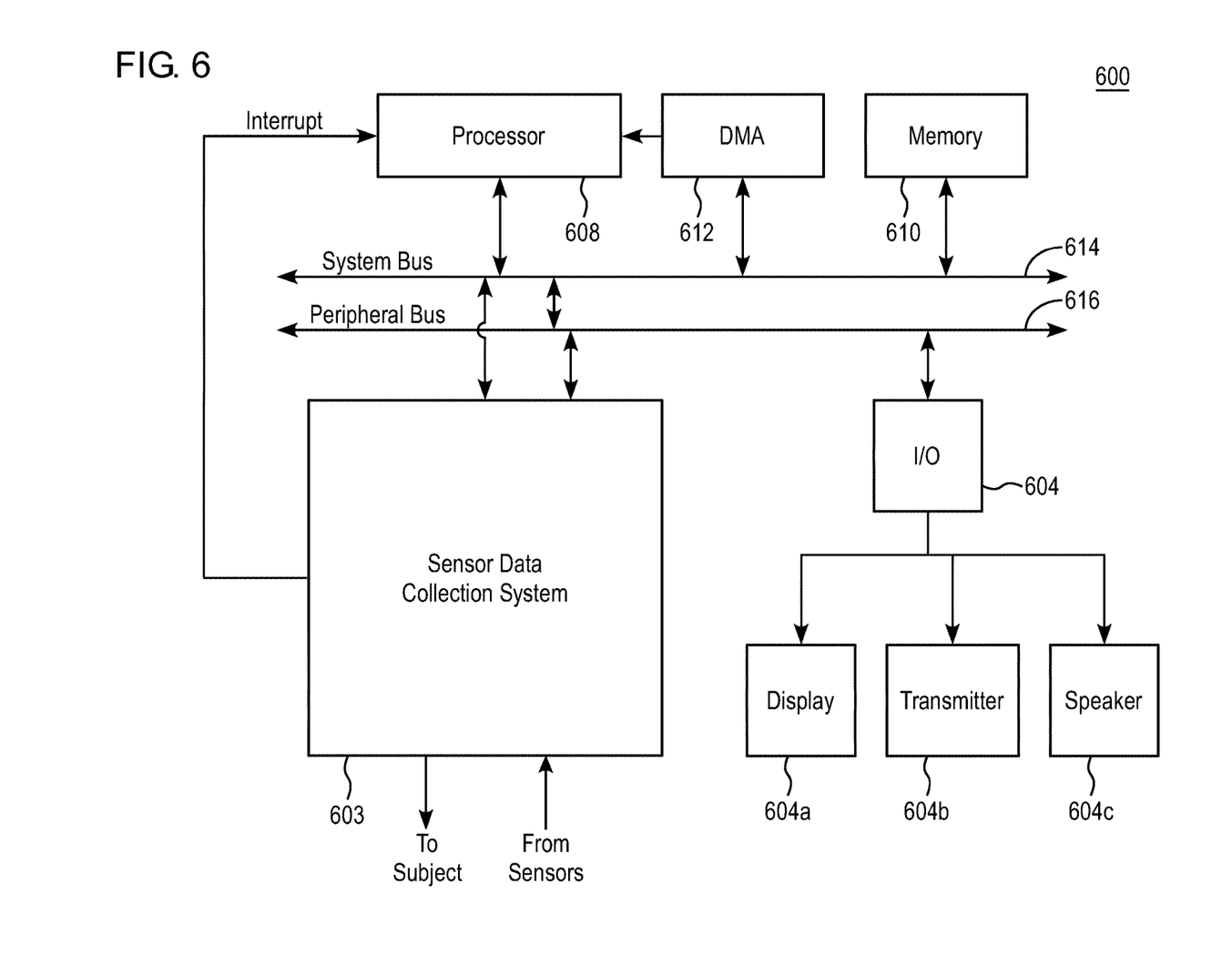
FIG. 6 illustrates an example of a system 600 that may implement monitoring in accordance with one or more embodiments described herein.

FIG. 6 illustrates an example of a system 600 that may implement monitoring in accordance with one or more embodiments described herein. System 600 may include a sensor data collection system 603, processor 608, system memory 610, DMA 612, system bus 614, and peripheral bus 616 corresponding structurally and/or functionally, at least in part, to sensor data collection system 503, processor 508, system memory 510, DMA 512, system bus 514, and peripheral bus 516, respectively, shown in FIG. 5. System 600 may also include a display 604a, transmitter/transceiver 604b, speaker 604c, and/or other peripherals coupled to peripheral bus 616 via I/O interface(s) 604.

Operations described herein may be implemented using any suitable controller or processor, and software application, which may be stored on any suitable storage location or computer-readable medium. The software application, for example, may provide instructions that enable processor 508 (608) and/or ESS 512 to perform one or more operations described herein.

In one or more embodiments, the disclosed processing may be performed by the wearable device or by an external device including but not limited to a sensor/relay/cloud processor, a smartphone device, and/or a cloud computing system.

The electronic assembly or components thereof (such as the processing system and/or the sensor data collection system) may include or comprise one or more of SoC hardware (SoC HW), an operating system, hardware layer abstraction, debug layers, test modules, and device drivers. A nonlimiting example of a suitable SoC may include one or more of the following:

- ARC-610D 32-bit Microprocessor as Control Processor (e.g., processor 508).
- ARC-610D 32-bit Microprocessor with XY Memory for DSP Processing (e.g., DSP 524).
- AMBA 2.0 AHB Fabric with arbitration
- 2-UARTs for Bluetooth Low Energy (BTLE) connectivity and as debug interface.
- 2-SPI interfaces.
  - One dedicated 1.8v SPI interface for SPI-Flash.
  - One shared (4 cs) SPI interface for MEMS, Altimeter, Gyroscope etc.
- 1 I2C interface for Altimeter.
- 8-Channel DMA Engine on AHB.
- ADC interface and Buffer (e.g., buffer 526) on AHB.
- Programmable Event Scheduler (e.g., ESS 518) to schedule sensor setup and data collection.
- 128-bit or 256-bit AES CCM Engine for data Encryption and Decryption.
- Power Management Unit.
- Event Scheduler (e.g., ESS 518) to independently manage and schedule ADC data capture.

An example of an ARC-610D 32-bit microprocessor as control processor (e.g., processor 508) may have one or more of the following (no limitation should be inferred):

- 64 KB Closely-Coupled Data Memory (DOOM).
- 128 KB Closely-Coupled Instruction Memory (ICCM) SRAM and 64 KB ROM
- 4-Port Register File.
- 32×32 Multiplier.
- Normalize
- Swap SmaRT for real trace function with an 8 Entry stack.
32-bit AHB Master.
JTAG debug interface.
AHB-DMI Slave interface to ICCM and DOOM.
29 External interrupts (31:3).

An example of an ARC-610D 32-bit microprocessor with XY Memory for DSP Processing (e.g., DSP 524) may have one or more of the following (no limitation should be inferred):

64 KB Closely-Coupled Data Memory (DCCM).
256 KB Closely-Coupled Instruction Memory (ICCM) SRAM and 32 KB ROM.
4-Port Register File
32×32 Multiplier (1 cycle).
Normalize
Swap
SmaRT for real trace function with an 8 entry stack.
32×16d16 XMAC (multiply & accumulate).
XY Memory (Single Bank of 4K bytes of X and Y)
32-bit AHB Master.
JTAG debug interface.
AHB-DMI Slave interface to ICCM and DCCM.
28 External interrupts (31:4).

One of ordinary skill in the art readily recognizes that and other components can be coupled to each other in a variety of different ways and configurations or can be stand-alone devices within the spirit and scope of the present invention.

A monitoring system has been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

Operations described herein may be implemented using any suitable controllers or processors, and software applications, which may be stored on any suitable storage location or computer-readable medium. The software application provides instructions that enable the processors or controllers to perform the operations described herein.

Furthermore, embodiments may take the form of a computer program product accessible from a computer-usable or computer-readable medium providing program code for use by or in connection with a computer or any instruction execution system. For the purposes of this description, a computer-usable or computer-readable medium can be any apparatus that can contain, store, communicate, propagate, or transport the program for use by or in connection with the instruction execution system, apparatus, or device.

The medium may be an electronic, magnetic, optical, electromagnetic, infrared, semiconductor system (or apparatus or device), or a propagation medium. Examples of a computer-readable medium include a semiconductor or solid state memory, magnetic tape, a removable computer diskette, a random access memory (RAM), a read-only memory (ROM), a rigid magnetic disk, and an optical disk. Current examples of optical disks include DVD, compact disk-read-only memory (CD-ROM), and compact disk-read/write (CD-R/W).

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A monitoring system, comprising:
   a sensor data collection system configured to control collection of sensor data related to one or more characteristics of a subject, including:
   a system bus;
   a peripheral bus;
   a scheduler, coupled to the system bus via the peripheral bus, configured to control sequencing and scheduling of the sensor data collection; and
   a buffer configured to receive and buffer data corresponding to the sensor data collected from one or more sensors in accordance with a signal provided by the scheduler; and
   one or more processors configured to:
   receive the buffered data from the buffer in accordance with a wake signal;
   process the received data; and
   output the processed data;
   wherein the sequencing and scheduling of the sensor data collection by the sensor data collection system is decoupled from the one or more processors;
   wherein the one or more processors are configured to enter a low-power sleep mode during the sensor data collection by the sensor data collection system, the low-power sleep mode preventing the one or more processors from the receive the buffered data, the process the received data, and the output the processed data;
   wherein the one or more processors are configured to exit the low-power sleep mode and resume the receive the buffered data from the buffer in accordance with the wake signal; and
   wherein in response to the buffer being full, the buffer provides the wake signal to the one or more processors.

2. The monitoring system of claim 1, further comprising:
   an analog-to-digital converter (ADC) configured to receive analog sensor data, convert the analog sensor data into digital sensor data, and output the digital sensor data in accordance with the first signal;
   wherein the data received and buffered by the buffer includes the digital sensor data output by the ADC.

3. The monitoring system of claim 2, further comprising:
   a transmitter configured to receive and transmit the processed data output by the one or more processors.

4. The monitoring system of claim 3, further comprising:
   the one or more sensors configured to provide the sensor data; and
   a base configured to support the one or more sensors, the sensor data collection system, and the one or more processors.

5. The monitoring system of claim 4, further comprising:
   a transmitter configured to receive and transmit the processed data output by the one or more processors;
   wherein the base is configured to support the transmitter.

6. The monitoring system of claim 4, further comprising:
   one or more batteries configured to supply power to the sensor data collection system and the one or more processors;
   wherein the one or more batteries are supported by the base.

7. The monitoring system of claim 4, wherein the one or more sensors include an ECG sensor and a respiratory sensor.

8. The monitoring system of claim 1, wherein the wake signal is provided to the one or more processors in accordance with an external interrupt.

9. The monitoring system of claim 1, wherein the wake signal is provided to the one or more processors in accordance with expiration of a timer.

10. The monitoring system of claim 1, wherein the sensor data collection system further includes a register control coupling the scheduler to the peripheral bus.

11. A wearable device, comprising:
a base; and
an electronic assembly supported by the base;
wherein the electronic assembly includes:
   a sensor data collection system configured to control collection of sensor data related to one or more characteristics of a subject, including:
      a system bus;
      a peripheral bus;
      a scheduler, coupled to the system bus via the peripheral bus, configured to control sequencing and scheduling of the sensor data collection; and
      a buffer configured to receive and buffer data corresponding to the sensor data collected from one or more sensors in accordance with a signal provided by the scheduler; and
   one or more processors configured to:
      receive the buffered data from the buffer in accordance with a wake signal;
      process the received data; and
      output the processed data;
wherein the sequencing and scheduling of the sensor data collection by the sensor data collection system is decoupled from the one or more processors;
wherein the one or more processors are configured to enter a low-power sleep mode during the sensor data collection by the sensor data collection system, the low-power sleep mode preventing the one or more processors from the receive the buffered data, process the received data, and output the processed data;
wherein the one or more processors are configured to exit the low-power sleep mode and resume receiving the buffered data in accordance with the wake signal; and
wherein in response to a buffer being full, the buffer provides the wake signal to the one or more processors.

12. The wearable device of claim 11, wherein the electronic assembly further includes:
an analog-to-digital converter (ADC) configured to receive analog sensor data, convert the analog sensor data into digital sensor data, and output the digital sensor data in accordance with the first signal;
wherein the data received and buffered by the buffer includes the digital sensor data output by the ADC.

13. The wearable device of claim 11, further comprising:
the one or more sensors configured to provide the sensor data; and
a base configured to support the one or more sensors, the sensor data collection system, and the one or more processors.

14. The wearable device of claim 13, further comprising:
a transmitter configured to receive and transmit the processed data output by the one or more processors;
wherein the base is configured to support the transmitter.

15. The wearable device of claim 13, further comprising:
one or more batteries configured to supply power to the sensor data collection system and the one or more processors;
wherein the one or more batteries are supported by the base.

16. The wearable device of claim 11, wherein the wake signal is provided to the one or more processors in accordance with an external interrupt.

17. The wearable device of claim 11, wherein the one or more sensors include an ECG sensor and a respiratory sensor.

* * * * *